United States Patent
Uitenbroek et al.

(10) Patent No.: US 6,827,806 B2
(45) Date of Patent: Dec. 7, 2004

(54) METHOD FOR MAKING AN ABSORBENT ARTICLE WITH PRINTED ELASTOMERS

(75) Inventors: Duane Girard Uitenbroek, Little Chute, WI (US); John Philip Vukos, Neenah, WI (US); Michael Tod Morman, Alpharetta, GA (US); Thomas Harold Roessler, Menasha, WI (US); Thomas Walter Odorzynski, Green Bay, WI (US); Michael Joseph Garvey, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 168 days.

(21) Appl. No.: 10/024,992

(22) Filed: Dec. 19, 2001

(65) Prior Publication Data

US 2003/0111166 A1 Jun. 19, 2003

(51) Int. Cl.$^7$ .......................... B32B 31/12; A61F 13/15

(52) U.S. Cl. ................. 156/229; 156/160; 156/163; 156/277; 442/328

(58) Field of Search .................. 156/229, 177, 156/191, 161, 160, 163, 164, 166, 176, 277; 604/385.24, 386; 442/328

(56) References Cited

U.S. PATENT DOCUMENTS

| | | | |
|---|---|---|---|
| 4,055,182 A | * 10/1977 | Mack | .............. 604/365 |
| 4,239,578 A | 12/1980 | Gore | |
| 4,364,787 A | 12/1982 | Radzins | |
| 4,379,016 A | 4/1983 | Stemmler et al. | |
| 4,381,781 A | 5/1983 | Sciaraffa et al. | |
| 4,397,704 A | 8/1983 | Frick | |
| 4,407,284 A | 10/1983 | Pieniak | |
| 4,464,217 A | 8/1984 | Dickover et al. | |
| 4,515,595 A | 5/1985 | Kievit et al. | |
| 4,618,384 A | 10/1986 | Sabee | |
| 4,663,220 A | 5/1987 | Wisneski et al. | |
| 4,704,116 A | 11/1987 | Enloe | |
| 4,710,189 A | 12/1987 | Lash | |
| 4,798,603 A | 1/1989 | Meyer et al. | |
| 4,808,176 A | 2/1989 | Kielpikowski | |
| 4,816,026 A | 3/1989 | Richardson | |

(List continued on next page.)

FOREIGN PATENT DOCUMENTS

| | | |
|---|---|---|
| EP | 217 032 | 4/1987 |
| EP | 417 766 | 3/1991 |
| EP | 437 771 | 7/1991 |
| EP | 650 714 | 5/1995 |
| EP | 682 930 | 11/1995 |
| EP | 750 893 | 1/1997 |
| EP | 820 747 | 1/1998 |
| EP | 1 179 330 | 2/2002 |
| EP | 1 188 427 | 3/2002 |
| EP | 1 228 741 | 8/2002 |
| WO | 95/16425 | 6/1995 |
| WO | WO 96/10481 | 4/1996 |
| WO | WO 00/38911 | 7/2000 |
| WO | WO 01/15646 A1 | 3/2001 |
| WO | 01/91685 | 12/2001 |
| WO | 01/92013 | 12/2001 |

*Primary Examiner*—Sue A. Purvis
(74) *Attorney, Agent, or Firm*—Pauley Petersen & Erickson

(57) ABSTRACT

The present invention provides a method of placing elasticized areas in a nonwoven web construction such as may be suitable for the waistbands or leg openings of disposable absorbent pant garments, cuffs on sleeves of medical garments, or the like. A web, or webs, of extendible nonwoven material which make up the substrate for the elasticized area are printed with an elastic adhesive in its fluid or semi-fluid and untensioned state to provide a tensioning force against distension of the web during wearing of the garment for conformable, well fitting, elasticized cuff areas and may further be used to reinforce biaxially extendible web components such as the backsheet web.

18 Claims, 5 Drawing Sheets

U.S. PATENT DOCUMENTS

| | | |
|---|---|---|
| 4,925,520 A | 5/1990 | Beaudoin et al. |
| 4,938,753 A | 7/1990 | Van Gompel et al. |
| 4,938,821 A | 7/1990 | Soderlund et al. |
| 4,965,122 A | 10/1990 | Morman |
| 4,968,313 A | 11/1990 | Sabee |
| 5,167,897 A | 12/1992 | Weber et al. |
| 5,176,668 A | 1/1993 | Bernardin |
| 5,176,672 A | 1/1993 | Bruemmer et al. |
| 5,192,606 A | 3/1993 | Proxmire et al. |
| 5,226,992 A | 7/1993 | Morman |
| 5,254,111 A | 10/1993 | Cancio et al. |
| 5,340,424 A | 8/1994 | Matsushita |
| 5,364,382 A | 11/1994 | Latimer et al. |
| 5,399,219 A | 3/1995 | Roessler et al. |
| 5,407,507 A | 4/1995 | Ball |
| 5,415,644 A | 5/1995 | Enloe |
| 5,429,629 A | 7/1995 | Latimer et al. |
| 5,486,166 A | 1/1996 | Bishop et al. |
| 5,490,846 A | 2/1996 | Ellis et al. |
| 5,496,298 A | 3/1996 | Kuepper et al. |
| 5,509,915 A | 4/1996 | Hanson et al. |
| 5,531,729 A | 7/1996 | Coles et al. |
| 5,540,796 A | 7/1996 | Fries |
| 5,595,618 A | 1/1997 | Fries et al. |
| 5,649,919 A | 7/1997 | Roessler et al. |
| 5,700,255 A | 12/1997 | Curro et al. |
| 5,827,259 A | 10/1998 | Laux et al. |
| 5,846,232 A | 12/1998 | Serbiak et al. |
| 5,910,224 A | 6/1999 | Morman |
| 6,049,023 A * | 4/2000 | Blenke et al. ............ 604/365 |
| 6,050,985 A | 4/2000 | Lavon et al. |
| 6,077,254 A | 6/2000 | Silwanowicz et al. |
| 6,149,638 A * | 11/2000 | Vogt et al. ............ 604/385.01 |
| 6,156,421 A | 12/2000 | Stopper et al. |
| 6,183,847 B1 | 2/2001 | Goldwasser |
| 6,231,557 B1 | 5/2001 | Krautkramer et al. |
| 6,245,050 B1 | 6/2001 | Odorzynski et al. |

* cited by examiner

METHOD FOR MAKING AN ABSORBENT ARTICLE WITH PRINTED ELASTOMERS

BACKGROUND OF THE INVENTION

It is desirable that personal care absorbent articles, and especially garments such as diapers, training pants, or incontinence garments, without limitation referred to generically now for ease of explanation as "diapers", provide a close, comfortable fit about the waist and legs of the wearer and contain body exudates while maintaining skin health. In certain circumstances, it is also desirable that such garments are capable of being pulled up or down over the hips of the wearer to allow the wearer or care giver to easily pull the article on and easily remove the article. Other garment openings such as sleeve or pant cuffs and necklines may benefit from similar elasticizing.

Various schemes for producing elastic waistbands on disposable diapers have been proposed. Diaper waistbands are generally made by stretching an elastomer, applying the stretched elastomer to the diaper components, typically non-elastic in the waistband area, and allowing the elastomer to retract, thus gathering the attached diaper web components in the waistband area. The gathered waistband will then ungather when applied to a wearer, to give the waistband circumference some extension while the elastomer produces a retractive force holding the waistband snug to the wearer.

In a known method of providing elasticized body openings for absorbent garments, U.S. Pat. No. 5,846,232 issued Dec. 8, 1998 to Serbiak et al., teaches the patterned application of elastic polymers between an extensible outer cover and an extensible bodyside liner and the application of solid waist and leg elastomers in a tensed condition to provide for elasticized areas in an absorbent article.

Elastomeric films have been developed which are desirable in several aspects for the manufacture of absorbent garments. As disclosed in U.S. Pat. No. 6,245,050, issued 12, Jun. 2001 to Odorzynski et al., an elastomeric film for use in disposable absorbent articles is taught which is a pressure sensitive adhesive and which provides liquid barrier properties with some vapor transmission. These films are hot melt extruded pressure-sensitive adhesives sometimes referred to as EBA (Elastic Barrier Adhesive).

In another known method of making elastic waist bands, U.S. Pat. No. 4,968,313 issued Nov. 6, 1990 to Sabee, teaches the application of a relaxed elastic element to a relaxed diaper web component which is subsequently drawn or stretched to change the molecular orientation of the fibers of the web and permanently deform the fiber structure to produce a gathered waist band for the garment.

However, the gathered-material waistband arrangements of the known art may apply excessive force to the skin of the wearer resulting in discomfort, red marks on the skin and other undesirable effects. There further remains a need for other methods of making waistbands for disposable garments which provide a more conformable fit to the wearer at the waist and leg openings. There further remains a need in the art to provide ease and economy of manufacture of absorbent garments, especially where such garments are intended to be disposable.

SUMMARY OF THE INVENTION

In response to the above discussion, an alternative method of elasticized garment opening construction is provided by the present invention which provides precise localized application of elastomerics to an extendible garment web for providing a tensioning force against distension of the web during a wearing, thereby creating a conformable fit to the wearer at the waist and leg openings, while maintaining ease and economy of manufacture, and adequate performance against leakage. The method may provide for the placement of variously shaped elastomer areas in a variety of orientations on a precursor garment web. The method according to one embodiment of the present invention provides for the printing, extrusion, or spraying application (hereinafter referred to collectively as "printing") of an elastic adhesive in a liquid or semi-liquid state to create elasticized areas in the leg and waist elastic regions of an extensible backsheet or top sheet. In another aspect of the invention the elastomers are utilized as vapor permeable liquid barrier materials that are flexible. In another aspect, the invention provides for the printing of an untensioned elastomeric material resulting in an elasticized portion of a garment which is not gathered. In another aspect, the printed elastomers serve to reinforce a biaxially extendible backsheet, i.e. a backsheet extendible in both longitudinal and lateral axes of the web. In another aspect, the elastomer serves as the adhesive between the topsheet and backsheet and further provides a vapor permeable liquid barrier.

The person having ordinary skill in the art of disposable diaper manufacture will appreciate that the disposable diaper is generally made up of the layers of a substantially liquid-impermeable backsheet, a liquid-permeable topsheet and a liquid retention structure located between the backsheet and the topsheet. In order to be extendible, any two joined layers must have compatible stretch to the limits of the desired processing parameters. In other words, the combined layers or webs, in those areas where the webs are fastened together, will be limited in the amount they may be stretched by the properties of the layer having the least amount of stretch.

The present invention presents an alternative way of making waistband and leg cuff elements by applying untensioned elastomers to the waistband and leg hole areas of the precursor garment, by way of printing the elastomer onto a web of extensible backsheet or topsheet material during the converting of the webs to a precursor garment web. The waistband and leg area diaper components of the present invention may be inherently extendible in the lateral, or longitudinal, or both, dimensions of the garment. The areas of the web having leg and waist elastomers may be extendible in either of the elastic sense i.e., with recovery; or the extensible sense, with little or no recovery. The elastomer is applied in an unstretched condition to make the elasticized areas of the extendible precursor garment web and to achieve ungathered elasticized waistbands and leg openings, either of which may sometimes be referred to hereinafter as "cuffs". When the diaper is placed on the wearer, the cuffs will be physically caused to laterally expand, thus forming a desirable snug fitting cuff area having expandable dimension and elastic tension.

Also, if areas of the backsheet, or topsheet, or both, are left biaxially extendible in areas where subsequent diaper loading, such as by exudates from the wearer, may make them sag undesirably, the backsheet, or other component webs of the precursor garment, may be selectively reinforced by patterned printings of the elastomer. Such printings may assume various shapes of elastomer, e.g., circular, striped, rectangular, etc., in various patterns on the web.

Generally, an exemplary embodiment of the present invention provides a disposable absorbent article that defines a front waist section, a rear waist section, an intermediate section which extends between and connects the waist sections, a pair of laterally opposed side edges, a pair of longitudinally opposed waist edges, a longitudinal direction and a lateral direction. Elastic waistbands and leg opening are provided in a unique fashion with selected elastic barrier adhesive (EBA) materials providing elastic, liquid barrier, and adhesive properties. Extendible backsheet and topsheet materials are provided as the materials carrying the elasticized leg and waist cuffs to conform to the body of the wearer.

The absorbent article may also include other known components of diapers such as a pair of fasteners located on the laterally opposed side edges in one of the waist sections. In certain aspects, the disposable absorbent article may be provided in a prefastened, pant-like configuration such that the article can be pulled on or off over the hips of the wearer similar to conventional training pants. For example, the fasteners may refastenably attach the laterally opposed side edges in the front waist section to the laterally opposed side edges in the rear waist section to provide the pant-like, prefastened absorbent article prior to packaging the articles.

There are various ways to accomplish the present invention. For example, the diaper outer cover, or backsheet, and bodyside liner, or topsheet, or both, may be constructed to be extendible in the lateral dimension, shown generally herein as the cross machine direction (CD), and assembled into the precursor diaper. An untensioned elastomeric may be printed in the cuff regions of the topsheet or backsheet before joining the two in the diaper making process, i.e., converting the components into a garment.

A first exemplary embodiment of the present invention may include the precursor web having an extendible topsheet and an extendible backsheet with an elastomeric placed between them in at least one cuff area of the precursor garment. The extendible top sheet and backsheet may be elastic or extensible, or a combination thereof, to achieve selectable conformity of the garment to the wearer.

BRIEF DESCRIPTION OF THE DRAWINGS

The present invention will be more fully understood and further advantages will become apparent when reference is made to the following detailed description of the invention and the drawings, in which.

DEFINITIONS

Figure 1:
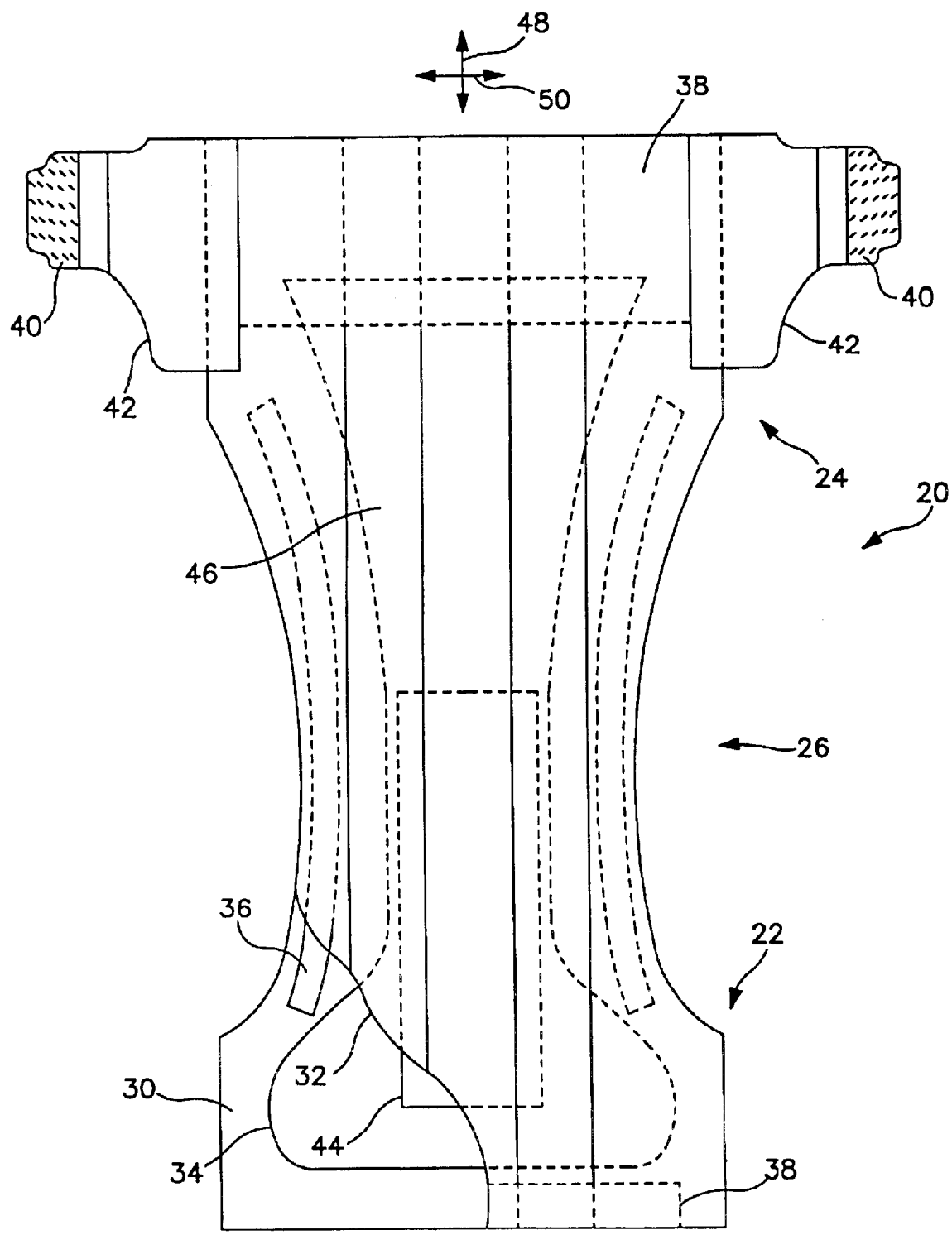
FIG. 1 representatively shows a partially cut-away, top plan view of the inward surface of an example of an article of the invention.

As used herein, the term "nonwoven web" or "nonwoven material" means a web having a structure of individual fibers, filaments or threads which are interlaid, but not in a regular or identifiable manner such as those in a knitted fabric or films that have been fibrillated. Nonwoven webs or materials have been formed from many processes such as, for example, meltblowing processes, spunbonding processes, and bonded carded web processes. The basis weight of nonwoven webs or materials is usually expressed in ounces of material per square yard (osy) or grams per square meter (gsm), and the fiber diameters usable are usually expressed in microns. (Note that to convert from osy to gsm, multiply osy by 33.91.) The term "fabrics" is used to refer to all of the woven, knitted and nonwoven fibrous webs.

As used herein, the terms "elastic", "elastomeric", and forms thereof, mean any material which, in its final form in the completed diaper, upon application of a biasing force, is stretchable, that is, elongatable, and which will return to substantially its original shape upon release of the stretching, elongating force. The term "extendible" refers to a material which is stretchable in at least one direction but which may or may not have sufficient recovery to be considered elastic. The term "extensible" refers to a material which is stretchable in at least one direction but which does not have sufficient recovery to be considered elastic.

As used herein, the term "machine direction", or MD, means the length of a fabric in the direction in which it is produced. The term "cross machine direction" or CD means the width of fabric, i.e. a direction generally perpendicular to the MD.

Words of degree, such as "about", "substantially", and the like are used herein in the sense of "at, or nearly at when given the manufacturing and material tolerances inherent in the stated circumstances" and are used to prevent the unscrupulous infringer from unfairly taking advantage of the invention disclosure where exact or figures or absolutes are stated as an aid to understanding the invention.

"Precursor" as used herein means those components, materials, assemblies, or the like which are used or exist in the making of a finished diaper before its completion as a commercially ready product.

"Printable adhesive" means an adhesive which may be applied in a liquid or semi-liquid state by any printing processes, extrusions, or sprayings, or other applications, which processes are collectively encompassed by the term "printing".

DETAILED DESCRIPTION OF THE PRESENTLY PREFERRED EMBODIMENTS

The various aspects and embodiments of the invention will be described in the context of disposable absorbent articles, and more particularly referred to, without limitation and by way of illustration only, as a disposable diaper. It is, however, readily apparent that the present invention could also be employed with other absorbent articles, such as feminine care articles, various incontinence garments, medical garments, and any other disposable garments, whether absorbent or not, needing an easily conformable cuff structure for elastic waistbands or leg open areas. Typically, the disposable articles or garments are intended for limited use and are not intended to be laundered or otherwise cleaned for reuse. A disposable diaper, for example, is discarded after it has become soiled by the wearer.

FIG. 1 is a representative plan view of an absorbent article, such as disposable diaper 20, of the present invention in its flat-out, or unfolded state. Portions of the structure are partially cut away to more clearly show the interior construction of the diaper 20. The surface of the diaper 20 which contacts the wearer is facing the viewer.

With reference to FIG. 1, the disposable diaper 20 generally defines a front waist section 22, a rear waist section 24, and an intermediate section 26 which interconnects the front and rear waist sections. The front and rear waist sections 22 and 24 include the general portions of the article which are constructed to extend substantially over the wearer's front and rear abdominal regions, respectively, during use. The intermediate section 26 of the article includes the general portion of the article that is constructed to cover the wearer's crotch region and extend between the legs. Thus, the intermediate section 26 is an area where repeated liquid surges typically occur in the diaper or other disposable absorbent article.

The diaper 20 includes, without limitation, an outer cover, or backsheet 30, a liquid permeable bodyside liner, or topsheet, 32 positioned in facing relation with the backsheet 30, and an absorbent body, or liquid retention structure 34, such as an absorbent pad, which is located between the backsheet 30 and the topsheet 32. The backsheet 30 defines a length, or longitudinal direction 48, and a width, or lateral direction 50 which, in the illustrated embodiment, coincide with the length and width of the diaper 20. The liquid retention structure 34 generally has a length and width that are less than the length and width of the backsheet 30, respectively. Thus, marginal portions of the diaper 20, such as marginal sections of the backsheet 30, may extend past the terminal edges of the liquid retention structure 34. In the illustrated embodiments, for example, the backsheet 30 extends outwardly beyond the terminal marginal edges of the liquid retention structure 34 to form side margins and end margins of the diaper 20. The topsheet 32 is generally coextensive with the backsheet 30 but may optionally cover an area which is larger or smaller than the area of the backsheet 30, as desired.

To provide improved fit and to help reduce leakage of body exudates from the diaper 20, the diaper side margins and end margins may be elasticized with suitable elastic members, as further explained below. For example, as representatively illustrated in FIG. 1, the diaper 20 may include leg elastics 36 which are constructed to operably tension the side margins of the diaper 20 to provide elasticized leg bands which can closely fit around the legs of the wearer to reduce leakage and provide improved comfort and appearance. Waist elastics 38 are employed to elasticize the end margins of the diaper 20 to provide elasticized waistbands. The waist elastics are configured to provide a resilient, comfortably close fit around the waist of the wearer.

Materials suitable for use as the leg elastics 36 and waist elastics 38 are particularly employed by the present invention to provide improved fit. Exemplary of such materials are printable, extruable, or sprayable elastomer adhesives, i.e. adhesives workable in a liquid or semi-liquid flowable state, such as the liquid impermeable, vapor permeable, hot melt, pressure-sensitive adhesives sometimes referred to as EBA (Elastic Barrier Adhesive). Variants of elastomeric materials suitable for use with the present invention may occur to the person having ordinary skill in the art upon gaining an understanding of the invention as presented herein and may include higher viscosity elastomers as well as very low viscosity elastomers such as latex emulsions.

As is known, fastening means, such as hook and loop fasteners, with a hook portion shown at ref. no. 40, may be employed to secure the diaper on a wearer. Alternatively, other fastening means, such as buttons, pins, snaps, adhesive tape fasteners, cohesives, fabric-and-loop fasteners, or the like, may be employed. In the illustrated embodiment, the diaper 20 includes a pair of side panels 42 to which the fasteners 40 are attached. Generally, the side panels 42 are attached to the side edges of the diaper 20 in one of the waist sections and extend laterally outward therefrom. The side panels 42 may be elasticized or otherwise rendered elastomeric. For example, the side panels 42 may be an elastomeric material such as a neck-bonded laminate (NBL) or stretch-bonded laminate (SBL) material. Methods of making such materials are well known to those skilled in the art and are described in U.S. Pat. No. 4,663,220 issued May 5, 1987 to Wisneski et al., U.S. Pat. No. 5,226,992 issued Jul. 13, 1993 to Morman, and European Patent Application No. EP 0 217 032 published on Apr. 8, 1987 in the names of Taylor et al. Examples of absorbent articles that include elasticized side panels and selectively configured fastener tabs are described in PCT Patent Application No. WO 95/16425 published Jun. 22, 1995 to Roessler; U.S. Pat. No. 5,399,219 issued Mar. 21, 1995 to Roessler et al.; U.S. Pat. No. 5,540,796 to Fries; and U.S. Pat. No. 5,595,618 to Fries.

The diaper 20 may also include a surge management layer 44, located between the topsheet 32 and the liquid retention structure 34, to rapidly except fluid exudates and distribute the fluid exudates to the liquid retention structure 34 within the diaper 20. Examples of suitable surge management layers 44 are described in U.S. Pat. No. 5,486,166 to Bishop and U.S. Pat. No. 5,490,846 to Ellis.

As representatively illustrated in FIG. 1, the disposable diaper 20 may also include a pair of containment flaps 46 which are configured to provide a barrier to the lateral flow of body exudates. The containment flaps 46 may be located along the laterally opposed side edges of the diaper 20 adjacent the side edges of the liquid retention structure 34. Each containment flap 46 typically defines an unattached edge which is configured to maintain an upright, perpendicular configuration in at least the intermediate section 26 of the diaper 20 to form a seal against the wearer's body. The containment flaps 46 may extend longitudinally along the entire length of the liquid retention structure 34 or may only extend partially along the length of the liquid retention structure 34. When the containment flaps 46 are shorter in length than the liquid retention structure 34 the containment flaps 46 can be selectively positioned anywhere along the side edges of the diaper 20 in the intermediate section 26. Such containment flaps 46 are generally well known to those skilled in the art. For example, suitable constructions and arrangements for containment flaps 46 are described in U.S. Pat. No. 4,704,96 issued Nov. 3, 1987, to K. Enloe.

The diaper 20 may be of various suitable shapes. For example, the diaper may have an overall rectangular shape, T-shape or an approximately hour-glass shape. In the shown embodiment, the diaper 20 has a generally I-shape. The diaper 20 further has a longitudinal direction 48, and a lateral direction 50. Other suitable components which may be incorporated on absorbent articles of the present invention may include waist flaps and the like which are generally known to those skilled in the art. Examples of diaper configurations suitable for use in connection with the instant invention which may include other components suitable for use on diapers are described in U.S. Pat. No. 4,798,603 issued Jan. 17, 1989, to Meyer et al.; U.S. Pat. No. 5,176,668 issued Jan. 5, 1993, to Bernardin; U.S. Pat. No. 5,176,672 issued Jan. 5, 1993, to Bruemmer et al.; U.S. Pat. No. 5,192,606 issued Mar. 9, 1993, to Proxmire et al., and U.S. Pat. No. 5,509,915 issued Apr. 23, 1996 to Hanson et al.

The various components of the diaper 20 are integrally assembled together employing various types of suitable attachment means, such as adhesive, ultrasonic bonds, thermal bonds, or combinations thereof. In one embodiment, for example, the topsheet 32 and backsheet 30 may be assembled to each other with the waist and leg area elastomeric adhesives, such as the hot melt, pressure-sensitive elastomeric adhesive EBA mentioned above, which thereby serve as both the elastic members 36 and 38, and at least a part of the attachment mechanism.

The illustrated diaper 20 includes distinctive waistband and leg cuff structures formed by applying an elastomeric 36, 38, respectively, to at least the backsheet 30 in a fluid or semi-fluid application process such as gravure or intaglio printing via a heated roller, screen printing, patterned extrusion, or spraying. The backsheet material is generally selected for superior feel, light weight, liquid impermeability, vapor permeability, and inherent hook attachment acceptance in a desirably embodiment of the present invention. The backsheet 30 can be composed of various materials that provide the desired property of extendibility and acceptance of the hot melt EBA of the exemplary embodiment. An outer surface of the garment may be produced with the spunbond facing serving as a fastening material for fabric loop type fasteners. The backsheet may be elastic or extendible. One such material is a 0.5 osy spunbond nonwoven comprising polyolefin or elastic polymers/filaments. The material is desirably extensible or elastic, dependent upon the particular application to which the personal care article is to be put.

As known in the art, the backsheet 30 generally includes a fabric or material layer which may be operatively attached or otherwise joined to the other diaper layers to extend over a major portion of the outward surface of the article. It will occur to the person having ordinary skill in the art that if the backsheet is not used in conjunction with the diaper waistband, other layers used in the construction of a diaper may be similarly utilized according to the precepts of the present invention. Generally, it is desirable for simplicity of construction that the backsheet 30 remains the structural unit of choice for applying the waistband and leg opening elastomerics in the making of diapers according to the present invention.

Desirably, the backsheet 30 is constructed to be permeable to at least water vapor. For example, in particular embodiments, the backsheet 30 may define a water vapor transmission rate (WVTR) according to the Mocon Water Vapor Transmission Rate Test of about 400 g/sq.m/24 hr. more or less, desirably at least about 1200 g/sq.m/24 hr, more desirably at least about 2000 g/sq.m/24 hr., and even more desirably at least about 3000 g/sq.m/24 hr. in the non-extended condition. In some embodiments, the backsheet 30 may define a WVTR of from about 400 to about 30,000 g/sq.m/24 hr. Materials which have a WVTR less than those above may not allow a sufficient amount of water vapor diffusion out of the diaper and undesirably result in increased levels of skin hydration. A Mocon WVTR test is described in U.S. Pat. No. 6,156,421 issued Dec. 5, 2000 to Stopper et al.

The topsheet 32, as representatively illustrated in FIG. 1, typically presents a body-facing surface that is compliant, soft-feeling, and non-irritating to the wearer's skin. Further, the topsheet 32 can be less hydrophilic than the liquid retention structure 34, and is sufficiently porous to be liquid permeable, permitting liquid to readily penetrate through its thickness to reach the absorbent composite. The topsheet layer 32 is typically employed to help isolate the wearer's skin from liquids held in the liquid retention structure 34.

Various woven and nonwoven fabrics can be used for topsheet 32. For example, the topsheet may be composed of a meltblown or spunbond web of the desired fibers, and may also be a bonded-carded-web. Layers of different materials that may have different fiber deniers can also be used. The various fabrics can be composed of natural fibers, synthetic fibers or combinations thereof. The topsheet 32 may be composed of a substantially hydrophobic material, and the hydrophobic material may optionally be treated with a surfactant or otherwise processed to impart a desired level of wettability and hydrophilicity. In a particular embodiment of the invention, topsheet 32 can be a nonwoven, spunbond polypropylene fabric composed of about 1.0–5.0 denier fibers formed into a web having a basis weight of about 0.5 osy and density of about 0.065 g/cc.

Desirably, the topsheet 32 is made from extendible materials for compatibility with the backsheet 30 as well as for reduced cost and improved manufacturing efficiency. Suitable extendible materials for use with the present invention may include nonwoven webs, woven materials and knitted materials. Such webs should be compatible with the printable adhesive elastomers according to the dictates of the present invention. Nonwoven fabrics or webs have been formed from many processes, for example, bonded carded web processes, meltblown processes and spunbond processes. The extendible material can be formed from at least one member selected from fibers and filaments of inelastic polymers. Such polymers include polyesters, for example, polyethylene terephthalate, polyolefins, for example, polyethylene and polypropylene, polyamides, for example, nylon 6 and nylon 66. These fibers or filaments are used alone or in a mixture of two or more thereof. Suitable fibers may also include natural and synthetic fibers as well as bicomponent, multi-component, and shaped polymer fibers. Many polyolefins are available for fiber production according to the present invention, for example, fiber forming polypropylenes include Exxon Chemical Company's Escorene7 PD 3445 polypropylene and Himont Chemical Company's PF-304. Polyethylenes such as Dow Chemical's ASPUN7 6811A linear low density polyethylene, 2553 LLDPE and 25355 and 12350 high density polyethylene are also suitable polymers. The nonwoven web layer may be bonded to impart a discrete bond pattern with a prescribed bond surface area.

Desirably, both the backsheet 30 and the topsheet 32 are extendible in the lateral direction as set forth above for improved fit and performance of the waistband and the overall garment. For example, a patterned layer of adhesive, applied by printing, spraying, or otherwise placing the adhesive as an array of separate lines, swirls, or spots, or other shapes of EBA may be used to affix the topsheet 32 to the backsheet 30. It should be readily appreciated that the above-described attachment mechanisms may also be employed to suitably interconnect, assemble and/or affix together the various other component parts of the garments or articles that are described herein.

The liquid retention structure 34 provides an absorbent structure for holding and storing absorbed liquids and other waste materials, such as the shown absorbent pad composed of selected hydrophilic fibers and high-absorbency particles. The liquid retention structure 34 may also be extendible or not extendible, although it should not interfere with the expanding of the waistband or leg cuff areas. The liquid retention structure 34 is positioned and sandwiched between the topsheet 32 and backsheet 30 to form the diaper 20. The liquid retention structure 34 has a construction that is generally compressible, conformable, non-irritating to the wearer's skin, and capable of absorbing and retaining body exudates. A spacer layer 54 (FIG. 2) may further be provided to act as a ventilation layer to insulate the backsheet 30 from the liquid retention structure 34 to reduce the dampness of the garment at the exterior surface of the backsheet 30.

Various types of wettable, hydrophilic fibrous material can be used to form the component parts of liquid retention structure 34. Examples of suitable fibers include naturally occurring organic fibers composed of intrinsically wettable material, such as cellulosic fibers; synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers; and synthetic fibers composed of a nonwettable thermoplastic polymer, such as polypropylene fibers, which have been hydrophilized by appropriate means. The fibers may be hydrophilized, for example, by treatment with silica, treatment with a material which has a suitable hydrophilic moiety and is not readily removable from the fiber, or by sheathing the nonwettable, hydrophobic fiber with a hydrophilic polymer during or after the formation of the fiber. For the purposes of the present invention, it is contemplated that selected blends of the various types of fibers mentioned above may also be employed. The liquid retention structure 34 can include a matrix of hydrophilic fibers, such as a web of cellulosic fluff, mixed with particles of high-absorbency material. In particular arrangements, the liquid retention structure 34 may include a mixture of superabsorbent hydrogel-forming particles or fibers and synthetic polymer meltblown fibers, or a mixture of superabsorbent particles or fibers with a fibrous coform material including a blend of natural fibers and/or synthetic polymer fibers.

The hydrophilic fibers and high-absorbency particles may be configured to form an average composite basis weight which is within the range of about 200–900 gsm. In certain aspects of the invention, the average composite basis weight is within the range of about 500–800 gsm, and alternatively is within the range of about 550–750 gsm to provide desired performance.

A substantially hydrophilic tissue wrapsheet is employed in the exemplary embodiment to help maintain the integrity of the fibrous structure of the liquid retention structure 34. The tissue wrapsheet is typically placed about the liquid retention structure over at least one major facing surface thereof and composed of an absorbent cellulosic material, such as creped wadding or a high wet-strength tissue that may or may not be pleated. In one aspect of the invention, the tissue wrapsheet can be configured to provide a wicking layer which helps to rapidly distribute liquid over the mass of absorbent fibers including the liquid retention structure 34. The wrapsheet material on one side of the absorbent fibrous mass may be bonded to the wrapsheet located on the opposite side of the fibrous mass to effectively entrap the liquid retention structure 34.

With reference to FIG. 1, each of the leg and waist elastic members 36, 38, respectively, is desirably a hot melt, pressure sensitive, adhesive, elastomeric applied by a printing or other liquid or semi-liquid based process. The disposable absorbent articles of the present invention may include at least one elasticized area formed from an elastomeric, hot melt, pressure-sensitive adhesive printed on one of the backsheet and the topsheet. The backsheet and topsheet components are adhered to the elastomeric, hot melt, pressure-sensitive adhesive. The elastomeric, hot melt, pressure-sensitive adhesive and the elasticized area formed therewith may have one or more of the following properties: an adhesive bond strength sufficient to adhere the backsheet and topsheet components during use of the disposable absorbent article; an elongation in one area of at least 25 percent; a retractive force in one area of less than 400 grams force per 2.54 cm (1.0 inch) width at 90 percent elongation; a viscosity of less than 70,000 centipoise at 177 degrees C.(350 degrees F.); and a cold flow value in one area of less than 20 percent at 54 degrees C.

As used herein, reference to an adhesive bond strength refers to the strength of the bond adhering first and second components together. The adhesive bond strength can be quantified by the amount of force required to separate the first and second components from one another according to the test method set forth below in connection with the examples. The elastomeric, hot melt, pressure-sensitive adhesive of the present invention suitably has an adhesive bond strength, as determined by the test method set forth below in connection with the examples, of at least 100 grams force per inch (2.54 cm) width, suitably of at least 200 grams force per inch (2.54 cm) width, alternatively of at least 400 grams force per inch (2.54 cm) width, alternatively of at least from about 200 grams force per inch (2.54 cm) width to about 700 grams force per inch width.

The elasticized area formed with the elastomeric, hot melt, pressure-sensitive adhesive suitably has at least a portion with an elongation of at least about 25 percent, alternatively of at least about 150 percent, alternatively of from about 50 percent to about 250 percent.

As used herein, reference to the retractive force of the elasticized area formed with the elastomeric, hot melt, pressure-sensitive adhesive refers to the retractive force exhibited by at least one portion of the elasticized area one minute after stretching to 90% of the elongation of the elasticized area, and is suitably determined as set forth below in connection with the examples. At least a portion of the elasticized area suitably has a retractive force of less than about 400 grams force per inch (2.54 cm) width, alternatively of less than about 275 grams force per inch (2.54 cm) width, alternatively of from about 100 grams force per inch (2.54 cm) width to about 250 grams force per inch (2.54 cm) width.

As used herein, reference to the viscosity of the elastomeric, hot melt, pressure-sensitive adhesive refers to the viscosity, in centipoise at 176 degrees C. (350 degrees F.) as determined by a Brookfield Model DV-III Programmable Rheometer (spindle size of 27) commercially available from E. Johnson Engineering & Sales Co., Elmhurst, Ill. 60126. A suitable test method is set forth in American Society for Testing and Materials (ASTM) test method D-3236. The elastomeric, hot melt, pressure-sensitive adhesives of the present invention suitably have a viscosity of less than 70,000 centipoise at 176 degrees C. (350 degrees F.), alternatively of less than 50,000, alternatively of from about 20,000 to about 35,000. This low viscosity enables the use of hot melt extrusion equipment which can be easier to use than typical thermoplastic material screw driven extrusion equipment.

Reference to the cold flow value of the elasticized area formed with the elastomeric, hot melt, pressure-sensitive adhesive refers to the amount of elastomer composite growth after the elasticized area has been exposed to a temperature of 54 degrees C. for a period of 24 hours. The cold flow values of the elasticized areas are suitably determined as set forth below in connection with the examples. At least a portion of the elasticized area formed with the elastomeric, hot melt, pressure-sensitive adhesives of the present invention suitably have a cold flow value of less than about 20 percent, alternatively of less than 15 percent, alternatively of from about 5 percent to about 10 percent.

A number of elastomeric components are known for use in the design and manufacture of disposable absorbent articles. For example, disposable absorbent articles are known to contain elasticized leg cuffs, elasticized waist portions, elasticized containment gaskets, and elasticized fastening tabs. Thus, with reference to FIG. 1, the elasticized areas of the disposable absorbent articles according to the present invention may form elasticized leg cuffs 36, waist elastics 38, elasticized fastening tabs 40, and elasticized containment gaskets 46. That is, the elastomeric, hot melt, pressure-sensitive adhesives of the present invention may be used in, or as, components of the disposable diapers to form, without limitation, the elasticized areas indicated as defining elasticized leg cuff 36, waist elastics 38, containment gaskets 46 and elasticized fastening tabs 42, respectively.

The disposable absorbent articles of the present invention need only have one elasticized area formed from an elastomeric, hot melt, pressure-sensitive adhesive. The elasticized areas are suitably formed by incorporating the hot melt, pressure-sensitive adhesive to one or more components of the disposable absorbent article. For example, the elasticized hot melt, pressure-sensitive adhesives may be applied to a first component such as the backsheet 30, the topsheet 32, or the absorbent structure 34, which first component may then be brought into contact with and adhered to a second component of the diaper by applying pressure to the adhesive. The second component may be a separate component or may be a different portion of the first component. For example, the elastomeric, hot melt, pressure-sensitive adhesive may be applied to the backsheet 30 which is then adhered to the topsheet 32 to form an elasticized area which functions as a leg 36 or waist 38 elastic, or the topsheet 32 may be folded in various manners to create integral leg cuffs with the adhesive contained therein.

Suitable elastomeric, hot melt, pressure-sensitive adhesives for the making of the films of the present invention comprise elastomeric polymers, tackifying resins, plasticizers, oils and antioxidants. Such elastomeric, hot melt, pressure-sensitive adhesives are available from Bostik-Findley, Inc., Wauwatosa, Wisconsin under the trade designations HX-2695-01, H2503, and H2504.

The leg and waist elastic members 36, 38, respectively, may have any of a multitude of configurations. For example, the width of the individual elastic members 36 may be varied from about 0.25 millimeters (0.01 inch) to about 38 millimeters (1.5 inch) or more. The elastic members may include a single strand of elastic material, or may include several parallel or non-parallel strands of elastic material, or may be applied in a rectilinear or curvilinear arrangement. Where the strands are non-parallel, two or more of the strands may intersect or otherwise interconnect within the elastic member. In particular embodiments of the invention, for example, three or four strands can be employed for each elasticized leg band.

PROCESSING EXAMPLE

The following example is presented to provide a more detailed understanding of the invention. The example is representative, and is not intended to limit the scope of the invention.

Figure 2:
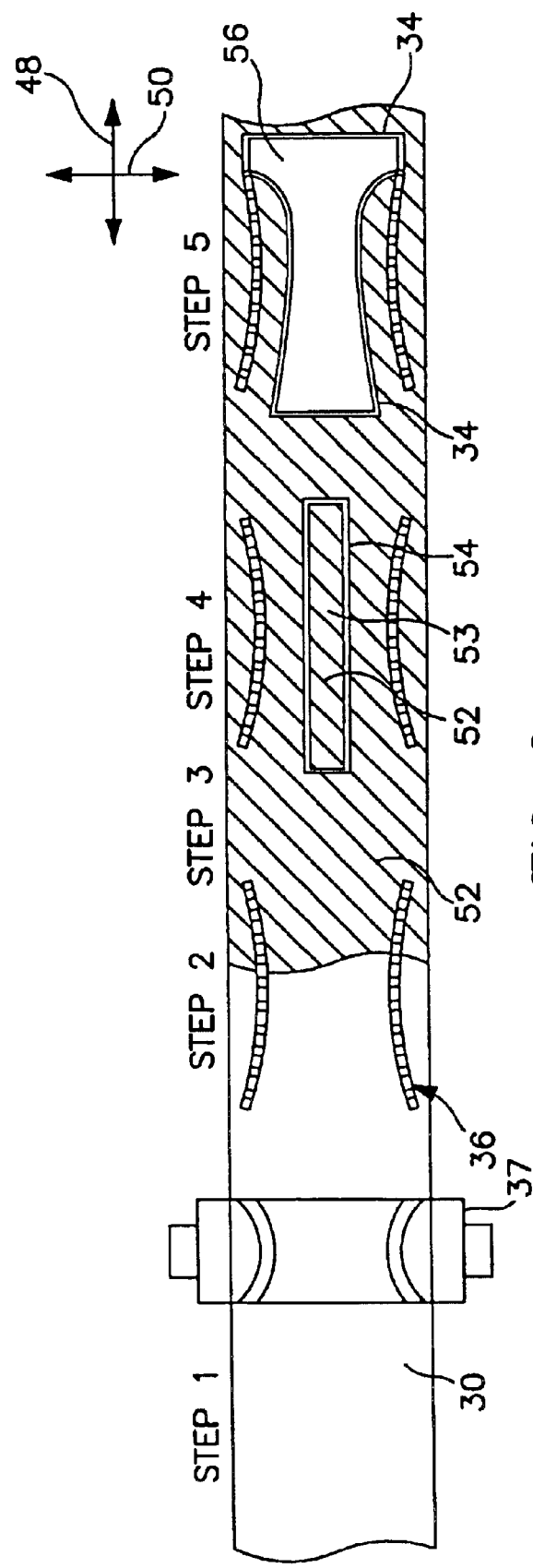
FIGS. 2–4 illustrate a manufacturing sequence of the conversion of various webs into disposable diapers according to the present invention with the longitudinal direction of the diapers being in the machine direction.
Figure 3:
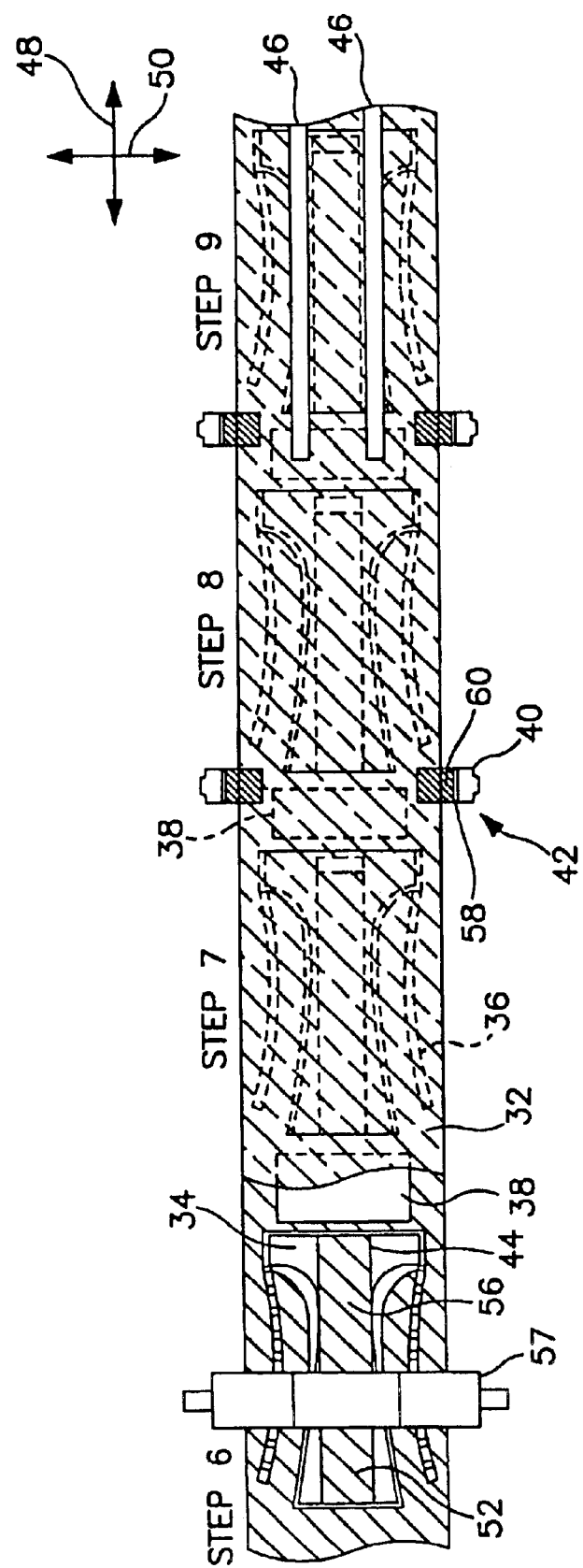
Figure 4:
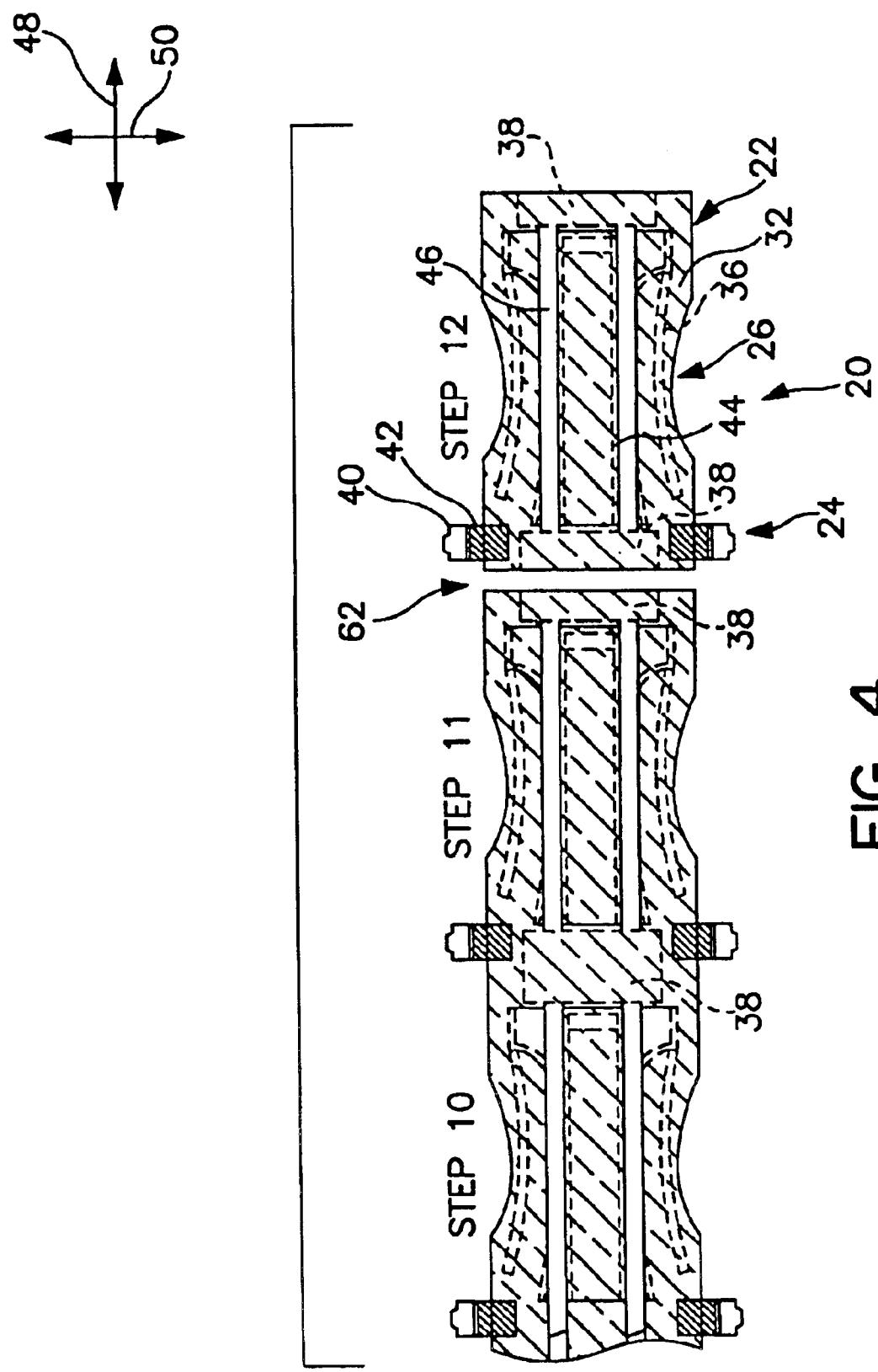

With reference to FIGS. 2–4, a method for constructing an absorbent article such as a disposable diaper according to the present invention may include the steps of constructing a precursor garment web and individuating the diapers therefrom as described below and as illustrated in FIGS. 2–4.

Referencing FIG. 2, in Step 1 a backsheet web 30, desirably, but not necessarily, including a web of substantially liquid impermeable and water vapor permeable material according to the above-described embodiment of FIG. 1, is fed into the garment making process as the foundation layer of the precursor garment web. The backsheet material 30 will expand in the lateral direction when force is applied in the lateral direction, and may, if desired, contract in the lateral direction after the force is removed.

In Step 2 unstretched leg elastic members 36 are applied to the top of backsheet material web 30 via a relief intaglio, or planographic roller 37, a printing screen, ink jetlike spray apparatus, or otherwise applied.

In Step 3 an adhesive 52, shown as diagonal lines, e.g., Disposamelt 34-5611, is applied to the backsheet material 30 by spraying or the like, desirably outside of the leg elastic member areas, should additional adhesive be desired for construction.

In Step 4 an adhesive 52 e.g., Disposamelt 34-5611, is applied to the top surface 53 of a spacer layer 54 e.g., a 0.8 osy spunbond meltblown spunbond nonwoven which is then applied to the backsheet material 30.

In Step 5 a liquid retention structure 34 e.g., including a composite fluff pad that is approximately a 60/40 blend of a superabsorbent material e.g., Favor SXM-880 and fiberized Fluff Pulp of 16% Hardwood is applied to the backsheet material 30. The liquid retention structure 34 may further be covered on its side to be adjacent to topsheet 32 (step 7) with a barrier tissue 56 e.g., American Tissue 12.5 pound white tissue. Additionally a forming tissue (not shown) e.g., white 9.79 pound per reel tissue may be positioned to cover the side of Liquid Retention (absorbent) structure 34 adjacent to the backsheet layer 30.

Referencing FIG. 3, in Step 6 a surge management layer 44 e.g., a through air bonded carded web (TABCW) nonwoven surge composite for the rapid uptake and channeling of liquids, is located operably adjacent to the liquid retention structure 34. Also in Step 6 an adhesive 52, e.g., Disposamelt 34-5611, may be applied to the top surface 56 of the surge management layer 44 by spraying, preplacement, or the like. Further, untensioned waist elastics 38 may then be applied, as by a heated intaglio roller 57, to the precursor garment web at the waistband regions of the precursor garments to provide for a flat waistband. In other embodiments the elastomeric may be printed on one the topsheet 32 or otherwise applied before this time.

In Step 7 a porous, liquid permeable, and laterally extendible top sheet web 32, indicated by broken cross hatching, is then applied and laminated to the layers of the precursor garment web and the adhesive elastic areas 36, 38 of the leg and waist areas, respectively. In Step 8 the provided side panels 42 having a fastening means 40 e.g., hook material such as VELCRO 851 hook, and carrier sheet 58 e.g., 1.25 osy SMS, and an elastic member 60 e.g., Necked Bonded laminate, may them be adhesively or ultrasonically laminated, or both, to the precursor garment web.

In Step 9 the containment flaps 46 may be adhesively laminated to the precursor garment web and have elastomeric materials e.g., two elastic strands (not shown) such as Glospan S7 Spandex fiber 700 denier (777 decitex). The flap elastic strands may be laminated to a nonwoven material e.g., blue SMS 0.65 osy to comprise the flaps 46.

Referencing FIG. 4, in Step 10 leg hole cut outs on the lateral margins of the precursor diaper will be seen as introduced in this step.

In Step 11, the precursor garment is then cut as at 62 into an individual resultant disposable diaper 20 as seen in Step 12. The diaper 20 can then be folded if desired (not shown).

Figure 5:
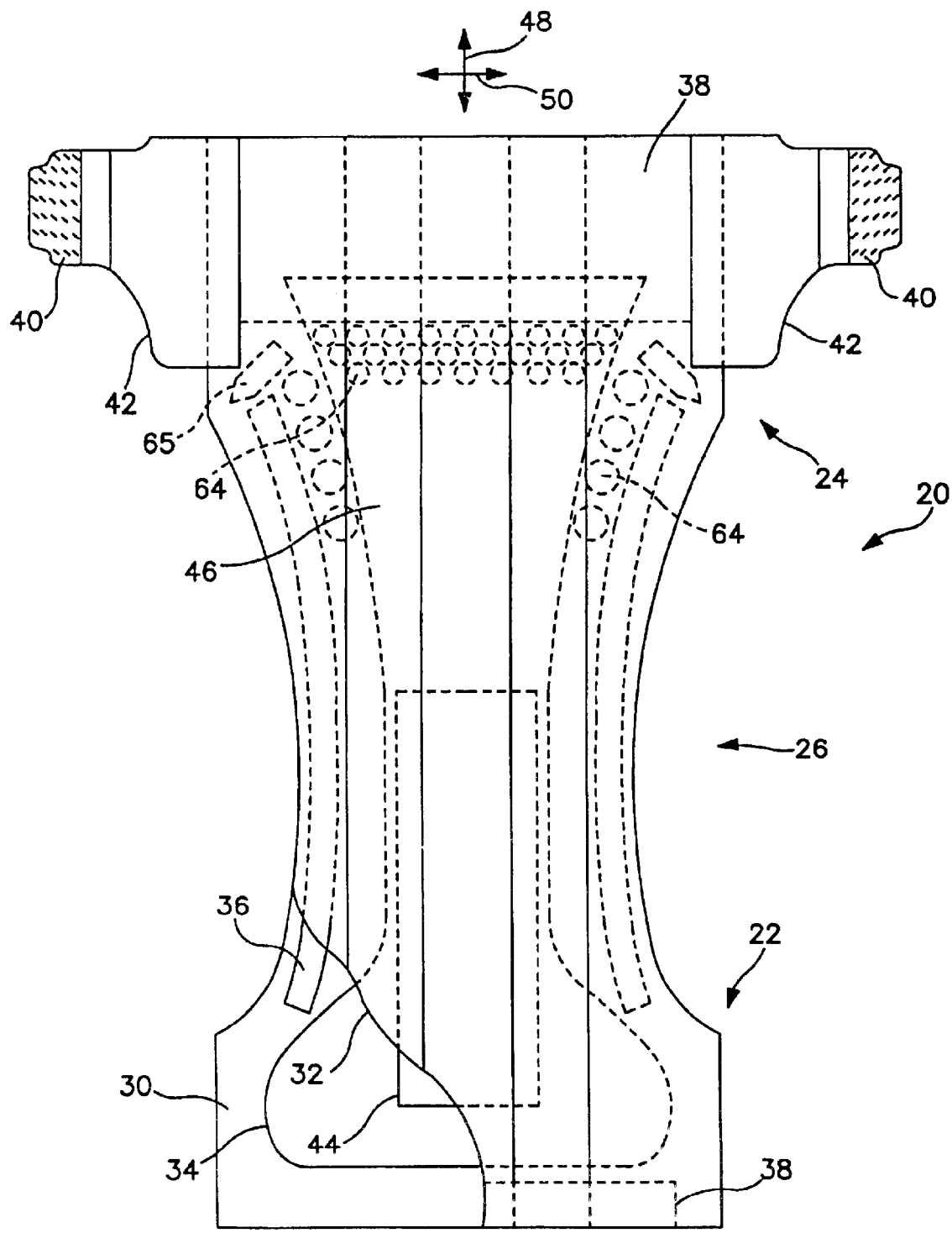
FIG. 5 illustrates a partially cut-away, top plan view of the inward surface of an example of an article of the invention similar to FIG. 1, but having had elastic adhesives pattern printed on the backsheet to reinforce the article.

Referencing FIG. 5, there is shown a partially cut-away, top plan view of the inward surface of an example of an article 20 of the invention similar to FIG. 1, but having had elastic adhesive deposits pattern printed on the backsheet to reinforce the article. The individual deposits of elastomer 64, while illustrated as circular deposits of various sizes, collectively 64, and elongated pentagonal deposits 65, may be of various shapes and sizes. Of particular interest are the and elongated pentagonal deposits 65 which will be noted as being placed off the lateral and longitudinal axes 50, 48 respectively, in order to act as a "dart" or control panel area in directions of the garment, or diaper 20, which are not restricted to the lateral or longitudinal directions of the diaper 20. Further, the illustrated pattern groupings and placements are intended as illustrative and are not intended to be limiting to the present invention. As illustrated, the elastomer deposits are suitably placed to reinforce the biaxially extendible backsheet 30 in the area of the rear waist section 24 which may sag when subject to loading of the diaper such as by the absorption of liquid exudates throughout the liquid retention structure 34. The reinforcing deposits may be printed with the same roller 57 as that used to print leg elastic elements 36 or may be printed with a different roller if desired.

It will thus be appreciated by those of skill in the art that the disposable diaper 20, as assembled using the proposed materials and methods of manufacture, has very easily placed leg elastic elements 36 and waist elastic elements 38 over that of conventional diaper designs. Also, the methods of the present invention may be used to make ungathered elastic cuff areas with good conformance to the wearer. Further, the leg elastic elements 36 and waist elastic elements 38 may provide a construction adhesive for the precursor diaper components and may act as a vapor permeable liquid barrier.

While the invention has been described in detail with respect to specific embodiments thereof, it will be appreciated that those skilled in the art, upon attaining an understanding of the foregoing may readily conceive of alterations to, variations of, and equivalents to these embodiments. Accordingly, the scope of the present invention should be assessed as that of the appended claims and any equivalents thereto.

We claim:

1. In a method of producing elastic areas on a precursor web suitable for making resultant absorbent garments, the steps comprising:
   printing the precursor web in an untensioned state with an untensioned elastic adhesive;
   the precursor web being extendible in an extendible direction;
   the untensioned elastic adhesive being printed in a shape or pattern sufficient to provide a tensioning force against web distension in the extendible direction of the precursor web; and
   constructing an absorbent garment from the precursor web with the elastic adhesive printed thereon remaining in the untensioned state; and
   wherein the elastic adhesive is printed as a pattern of shapes.

2. The method according to claim 1 wherein the precursor web comprises a backsheet web.

3. The method according to claim 2, wherein the backsheet web comprises at least one of a nonwoven spunbond web, a microporous film, and an elastomeric film, extendible in one or more directions of the absorbent garment.

4. The method according to claim 2, wherein the precursor web further comprises a topsheet web.

5. The method according to claim 2 wherein the backsheet comprises material selected from the group comprising, necked nonwovens, extendible films, elastomerics, or combinations thereof.

6. The method according to claim 1 wherein the precursor web comprises an assembled diaper lacking only a leg or waistband elastic.

7. The method according to claim 1 wherein the elastic adhesive material is a compound having vapor permeable liquid barrier properties.

8. The method according to claim 1 wherein the elastic adhesive material is retractable after elongation to a length substantially equivalent to the original length.

9. The method according to claim 1 wherein the elastic adhesive material has a cold flow value of less than 20 percent at 54 degrees C.

10. The method according to claim 1 wherein the elastic adhesive material has a viscosity of less than 70,000 centipoise at 177 degrees C. (350 degrees F.).

11. The method according to claim 1 wherein the elastic adhesive material has elongation of at least 25 percent.

12. The method according to claim 1 wherein the elastic adhesive material has refractive force of less than 400 grams force per 2.54 cm (1.0 inch) width at 90 percent elongation.

13. The method according to claim 1 wherein the printing is done via a heated roller.

14. The method according to claim 1 wherein the printing is done by at least one of the processes including relief intaglio, planographic, spraying, gravure, screening, and extrusion.

15. The method according to claim 1 wherein the precursor web is extendible in more than one direction.

16. The method according to claim 15 wherein the elastic adhesive is printed in selected patterns of shapes selected from at least one of lines, swirls, spots and elongated pentagonal deposits, for reinforcement of the precursor web.

17. The method according to claim 15 whereby the elastic adhesive pattern of shapes provides for reinforcement of the precursor web against distension of the web when the absorbent garment is loaded.

18. The method according to claim 1 wherein the elastic adhesive is printed in selected patterns of shapes selected from at least one of lines, swirls, spots and elongated pentagonal deposits, for reinforcement of the precursor web.

* * * * *

UNITED STATES PATENT AND TRADEMARK OFFICE
CERTIFICATE OF CORRECTION

PATENT NO. : 6,827,806 B2
DATED : December 7, 2004
INVENTOR(S) : Duane Girard Uitenbroek et al.

It is certified that error appears in the above-identified patent and that said Letters Patent is hereby corrected as shown below:

Column 14,
Line 34, delete "refractive" and insert -- retractive -- in place thereof.

Signed and Sealed this

Twenty-sixth Day of April, 2005

JON W. DUDAS
*Director of the United States Patent and Trademark Office*